United States Patent
Navis

(10) Patent No.: US 9,474,887 B2
(45) Date of Patent: Oct. 25, 2016

(54) SURGICAL IMPLEMENT GUIDE ASSEMBLY AND METHODS

(71) Applicant: Merit Medical Systems, Inc., South Jordan, UT (US)

(72) Inventor: John A. Navis, Oswego, IL (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 14/493,847

(22) Filed: Sep. 23, 2014

(65) Prior Publication Data

US 2015/0087914 A1 Mar. 26, 2015

Related U.S. Application Data

(60) Provisional application No. 61/881,807, filed on Sep. 24, 2013.

(51) Int. Cl.
*A61M 5/178* (2006.01)
*A61M 39/02* (2006.01)
*A61B 17/34* (2006.01)
*A61B 17/00* (2006.01)

(52) U.S. Cl.
CPC .......... *A61M 39/02* (2013.01); *A61B 17/3415* (2013.01); *A61B 17/3417* (2013.01); *A61B 17/3421* (2013.01); *A61B 17/3439* (2013.01); *A61B 2017/00477* (2013.01)

(58) Field of Classification Search
CPC ...................... A61B 17/3415; A61B 17/3403; A61B 2039/0229
USPC ........................................ 604/167.01–167.06
See application file for complete search history.

(56) References Cited

U.S. PATENT DOCUMENTS

| | | | | |
|---|---|---|---|---|
| 5,104,388 A | * | 4/1992 | Quackenbush | A61M 25/0668 604/164.05 |
| 5,413,561 A | * | 5/1995 | Fischell | A61M 39/0606 604/167.01 |
| 5,454,790 A | * | 10/1995 | Dubrul | A61M 25/0668 604/104 |
| 5,569,206 A | * | 10/1996 | Gorman, Jr. | A61B 17/3462 604/167.01 |
| 5,647,860 A | * | 7/1997 | Roth et al. | A61J 15/0023 604/264 |
| 5,938,582 A | * | 8/1999 | Ciamacco, Jr. | A61N 5/1002 600/3 |

(Continued)

FOREIGN PATENT DOCUMENTS

DE 20307557 10/2003
WO 2015047989 A1 4/2015

OTHER PUBLICATIONS

International Search Report and Written Opinion dated Jan. 14, 2015 for PCT/US2014/056908.

*Primary Examiner* — Ellen C. Hammond
*Assistant Examiner* — Stuart S Bray
(74) *Attorney, Agent, or Firm* — Stoel Rives LLP

(57) ABSTRACT

Features of guides and surgical implements, which may be utilized together in various assemblies, are disclosed. Surgical implements or other devices within the scope of this disclosure may include a circumferentially grooved knob. The knob may be configured to receive a portion of a guide. Further, a clip may be configured to releasably secure the guide to the surgical implement. The clip may be coupled to the knob, for example, by a strap rotatably coupled to the knob. The knob may also define a stop-ledge configured as an abutment for the guide. The knob may also define a central passageway, which may also be surrounded by a hollow hub, for receiving an additional surgical implement or device.

11 Claims, 3 Drawing Sheets

(56) References Cited

U.S. PATENT DOCUMENTS

| | | | | |
|---|---|---|---|---|
| 5,951,519 A * | 9/1999 | Utterberg | A61M 39/20 604/167.01 |
| 6,017,327 A * | 1/2000 | Wiklund | A61M 39/20 128/DIG. 26 |
| 6,589,212 B1 | 7/2003 | Navis | |
| 6,702,787 B2 * | 3/2004 | Pasqualucci | A61B 17/34 604/158 |
| 7,717,878 B2 | 5/2010 | Smith | |
| 8,273,060 B2 * | 9/2012 | Moreno, Jr. | A61B 17/3462 604/158 |
| 8,419,762 B2 * | 4/2013 | Delsman | A61B 17/3415 600/184 |
| 8,430,851 B2 * | 4/2013 | McGinley | A61B 17/3462 604/164.07 |
| 8,702,596 B2 * | 4/2014 | Kaye | A61B 1/00137 128/205.24 |
| 2003/0216771 A1 * | 11/2003 | Osypka | A61M 25/0668 606/191 |
| 2004/0111061 A1 * | 6/2004 | Curran | A61B 17/3421 604/174 |
| 2005/0124937 A1 * | 6/2005 | Kick | A61B 17/3417 604/164.1 |
| 2006/0253077 A1 * | 11/2006 | Smith | A61B 17/3421 604/167.06 |
| 2008/0300538 A1 * | 12/2008 | Schweikert | A61M 25/0097 604/99.04 |
| 2012/0116303 A1 * | 5/2012 | Marx | A61B 17/3415 604/98.01 |
| 2012/0158008 A1 * | 6/2012 | Garcia | A61B 17/3415 606/108 |
| 2012/0197087 A1 * | 8/2012 | Smith | H04L 41/5074 600/208 |

* cited by examiner

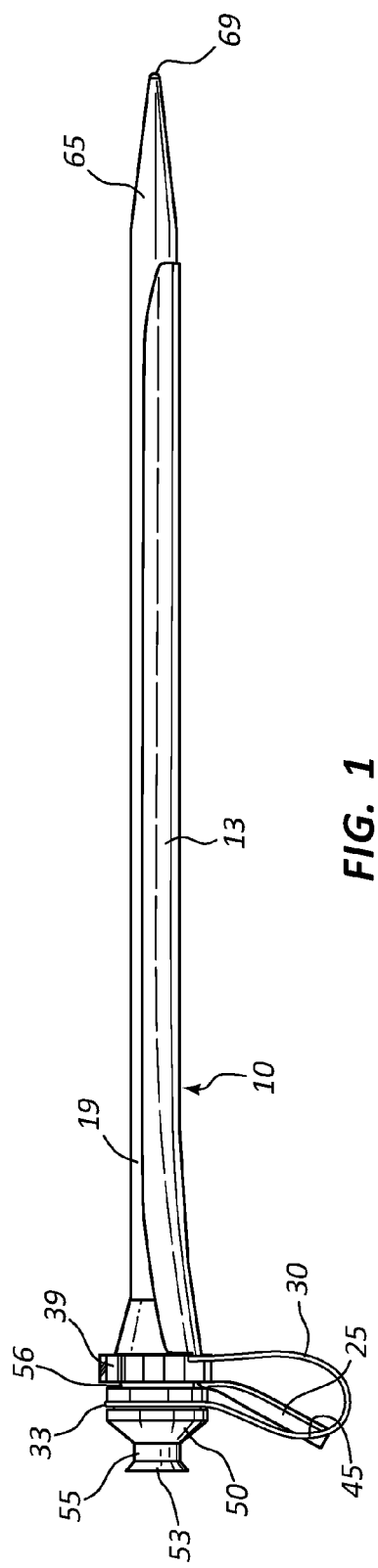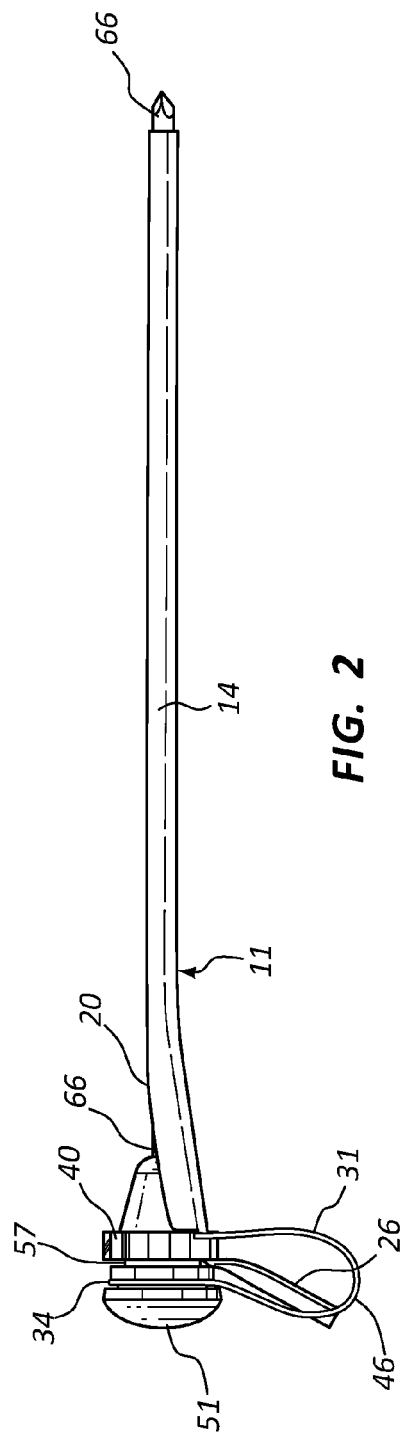

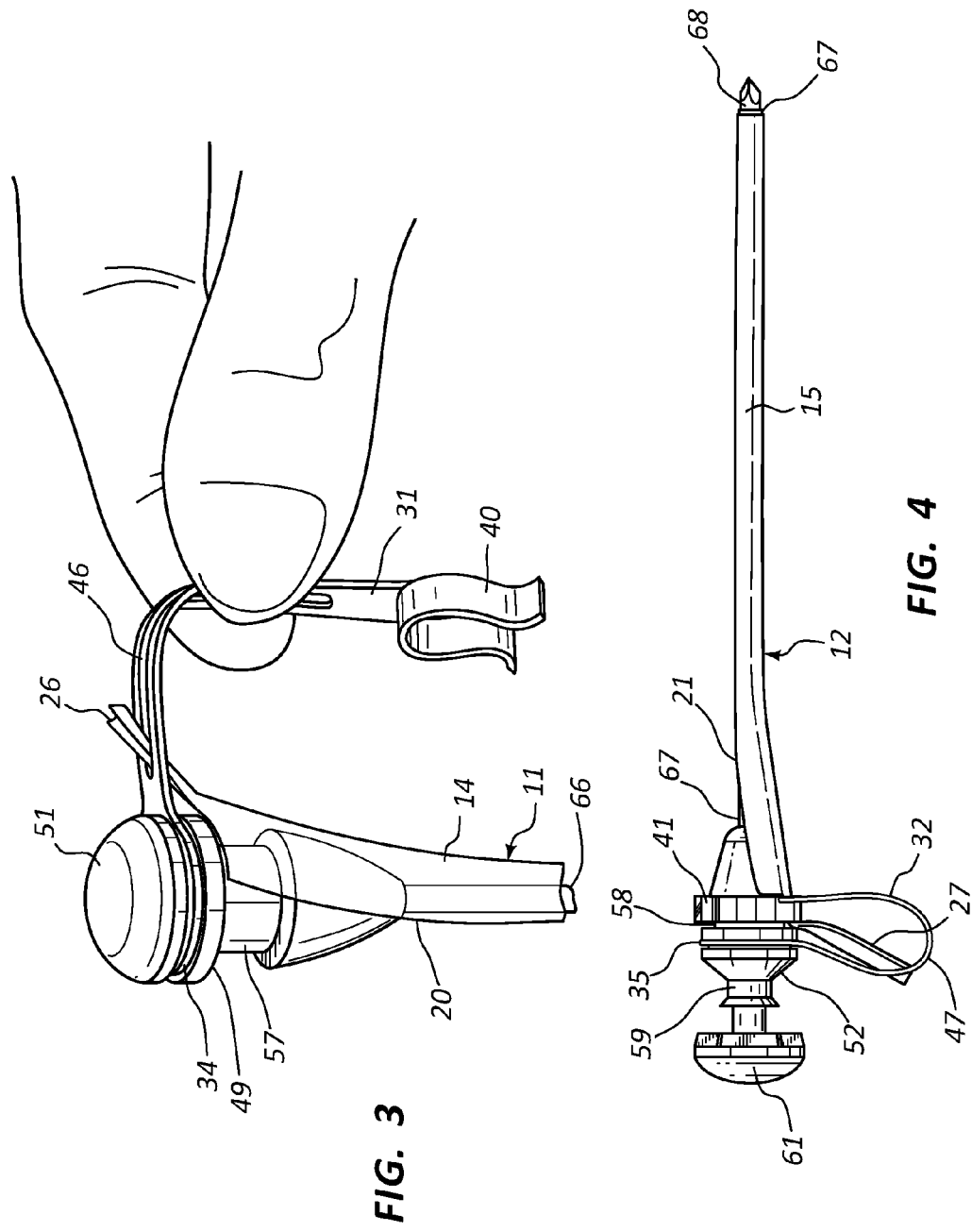

SURGICAL IMPLEMENT GUIDE ASSEMBLY AND METHODS

RELATED APPLICATION

This application claims priority to U.S. Provisional Application No. 61/881,807 filed on Sep. 24, 2013, titled SURGICAL IMPLEMENT GUIDE ASSEMBLY AND METHODS, the entire contents of which are hereby incorporated by reference.

TECHNICAL FIELD

The present disclosure relates to a surgical implement guide assembly used to percutaneously introduce surgical instruments, such as cannulae, trocars, dilators, and the like, into or through various portions of tissue, and/or naturally occurring orifices and/or naturally occurring ducts.

BRIEF DESCRIPTION OF THE DRAWINGS

FIG. 1 is a side view of an assembly comprising a dilator and a guide with a clip engaged to releasably secure the guide to the dilator.

FIG. 2 is a side view of an assembly comprising a trocar and a guide with a clip engaged to releasably secure the guide to the trocar.

FIG. 3 is a partial view of a proximal end of the assembly of FIG. 2 with the clip disengaged from the trocar.

FIG. 4 is a side view of an assembly comprising a cannula—with a knob having an outwardly extending hollow hub—a guide, and a trocar; a clip is engaged to releasably secure the guide to the cannula.

DETAILED DESCRIPTION

Figure 5:
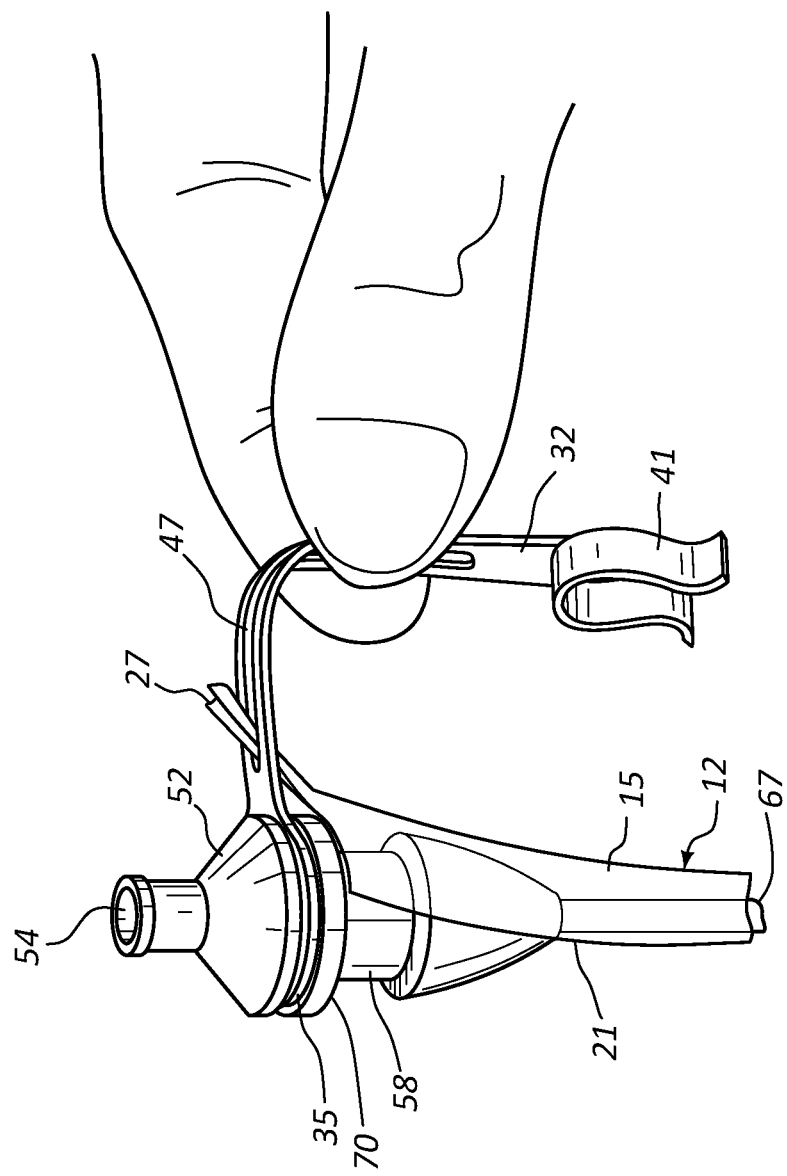
FIG. 5 is a partial view of a proximal end of the assembly of FIG. 4 with the trocar removed from the cannula and the clip disengaged from the cannula.

Surgical implement guides or sheaths may be used to facilitate percutaneous insertion and removal of surgical devices into openings in the body through various tissues. For example, insertion of catheters into blood vessels may be accomplished percutaneously. In some such procedures, a needle with a guidewire is used to initially enter the vessel, rather than use of a surgical cut-down procedure. Some procedures use the puncture needle itself as the direct conduit into the blood vessel (or other target site, such as the abdomen) for catheters of sufficiently small diameters.

In other procedures, metal sheaths and/or trocars may be used to facilitate access to a subcutaneous target. Certain sheaths may be formed with a slot, split into two distinct pieces, or otherwise configured to facilitate removal of the sheath. Furthermore, sheaths of various designs and configuration may be formed of plastic or other materials. Sheaths may be configured as thin-walled plastic sheaths. A "split sheath" is an example of a sheath configured to facilitate removal of the sheath. A split sheath includes a generally cylindrical sheath which may be formed in a range of diameters and lengths. The distal edge of the sheath may comprise a radius configured to form a smooth transition to a dilator, the distal end of which may be tapered to form a small diameter opening to permit passage of a guidewire. The proximal end of a split sheath may have two handles or finger grips formed on opposing sides of the sheath. Score marks formed along the length of the sheath may be configured to cause the sheath to split apart when the handles are pulled, facilitating the removal of the sheath from the body.

The Seldinger Technique may be utilized when implanting a catheter with the use of a split sheath. In this technique a needle is inserted into a blood vessel. A guidewire may then be inserted through the needle into the blood vessel and then the needle retracted, leaving the guidewire in place.

One or more dilators of increasing diameter may then be threaded over the guidewire into the blood vessel. The final such dilator, the dilator of the largest diameter, may have a split sheath affixed. The final dilator may be removed leaving the sheath in the blood vessel. The guidewire may also be removed. After all other components are removed, the sheath may be inserted approximately 70% to 80% within the vessel. The catheter may then be advanced through the sheath into the vessel. In some instances, depending on practitioner training or preference, certain steps may be performed in various sequences. For example, the guidewire/final dilator removal sequence may be reversed. In some procedures, the guidewire may be retained within the vessel until the catheter is in position.

Once the catheter is within the vessel, the sheath may then be removed. For some splitable sheaths, the physician grasps the handles and simultaneously pulls them apart one from the other, causing the sheath to split. While the sheath is being split, it may be simultaneously retracted from the blood vessel. In some instances retracting the sheath causes the catheter to be inadvertently retracted as well. A practitioner may stop removing the sheath to advance the catheter to its original position when removal of the sheath displaces the catheter. These steps may be repeated, adjusting both the catheter and the sheath, until the catheter is in the desired location and the sheath has been fully split and removed. Though this exemplary procedure describes accessing a blood vessel, analogous procedures may be utilized to gain access to various locations within the body, including, for example, vessels, lumens, openings, and cavities such as the peritoneal, thoracic, or other cavities.

Thus, the process of splitting and retracting the sheath and re-advancing or adjusting the catheter may be repeated until the sheath is totally removed, and the catheter fully and accurately positioned. If the catheter is inadvertently completely removed during the process, and/or the sheath is inadvertently removed before the catheter is placed, it may be necessary to repeat the entire process, beginning with the insertion of the needle.

During some procedures, the sheath may become covered with liquid, or otherwise become difficult to grasp. Thus, practitioners may need to use both hands to remove or split the sheath, leaving the catheter unsecured, unless an assistant is present. Further, in some instances, pulling on the sheath to remove it may cause it to tear prematurely.

Further, scored splitable sheaths are sized with a predetermined specific diameter which is not adjustable. These sheaths are made with a specific, fixed diameter; do not provide alternatives; and are not adaptable to accommodate different types of dilators, catheters, trocars, or instruments, or even patient situations.

Due to such concerns, guides or sheaths for surgical implements have been developed which include a shaft made of flexible material with memory to return to a predetermined configuration. Some such guides may be configured to temporarily have a new or different memory set into them. Thus, some guides may comprise an opening and passageway configured to be adjustable across a range between a predetermined minimum and maximum dimension. For example, the diameter of the guide may be extendable through the entire length of the shaft of the guide. Further the guide may include an elongated tab member which may have a textured surface extending from the shaft that acts as a handle for placing, removing, or controlling the guide. One such guide is shown in U.S. Pat. No. 6,589,212 to Navis.

Some such guides may be sized for insertion into tissue together with a surgical assembly. A guide may have a shaft of a flexible material with memory to return to its predetermined configuration. The shaft may be configured to receive a surgical implement such as a catheter in a passageway defined by the shaft. The shaft may further include an elongated tab member, such as a tab integral with the shaft, extending from the shaft that is used as a handle to place, control, and remove the guide.

Some of the features described above may allow the guide to shift relative to the surgical implement. The disclosure below may be configured to resist or eliminate shifting of these components.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations on a medical device, including surgical instruments such as needles, trocars, wires, guides, cannula, and so forth. The proximal end of a device is defined as the end closest to the practitioner when the device is being used by the practitioner. The distal end is the end opposite the proximal end, along the longitudinal direction of the device, or the end furthest from the practitioner when in use.

The term "knob" as used herein means a protuberance, such as a rounded protuberance, which may extend from an assembly component such as a surgical implement. For example, a rounded protuberance at one extremity of a surgical implement comprises a knob in some embodiments. Exemplary knobs may be solid or may be provided with a through passageway, for example, along the longitudinal direction of an elongate component. In some instances, a knob may also be provided with an outwardly extending hollow hub surrounding the passageway, for example, to facilitate introduction of another surgical implement therewithin, such as a trocar passing through a cannula.

The term "guide" as used herein refers to a medical device configured to at least partially direct or guide the placement of a secondary medical device. An introducer sheath is an example of a guide within this meaning. An introducer sheath may be placed in communication with a body lumen and facilitate passage of other components (i.e., guidewires, catheters, and so on) through the introducer sheath into the body lumen.

In one embodiment, the present disclosure relates to an assembly comprising a surgical implement provided with a strap rotatably attached to a rounded protuberance or knob adjacent a proximal end of the implement. A distal end of the strap is coupled to a clip configured to releasably engage a circumferential groove adjacent the knob. The proximal end of the strap is coupled adjacent the rounded protuberance. When the surgical implement is received into a guide, the clip can engage the knob, as well as a portion of the guide, such as a portion of a shaft of the guide, for example, to secure the guide to the knob. When the clip securing the guide to the knob is disengaged from the knob, the guide is released from the surgical implement and the surgical implement can be removed from the guide.

Another embodiment of the present disclosure comprises an elongated surgical implement with a knob at the proximal end thereof, the knob having a circumferential groove therein, and a strap rotatably coupled to the knob at a proximal end portion of the knob and terminating in a clip coupled adjacent the distal end of the strap; the clip may be configured to releasably engage the knob in the circumferential groove.

Further, yet another embodiment of the present disclosure comprises a surgical implement assembly comprising a hollow, flexible surgical implement guide with a tab member coupled to the guide, an elongated surgical implement having a knob at the proximal end thereof, and a strap rotatably attached to the knob. In some embodiments, the strap may terminate in a clip at the distal end of the strap. The clip may be configured to releasably engage the knob. When assembled in one exemplary configuration, the elongated surgical implement is at least partially surrounded by the guide and the clip may be engaged with the knob to secure the guide to the surgical implement. Further, in certain embodiments, the knob may also have a stop-ledge or other feature configured to interact with other components of the assembly to control relative displacement of the components. For example, a stop-ledge or shoulder on the knob may be configured to contact a portion of the guide, such as the proximal end thereof. In some embodiments, the proximal end of the guide may contact the stop-ledge when the components are assembled in an exemplary configuration. In this configuration, the stop-ledge can be configured to abut the guide to maintain or control the position of the proximal end of the guide with respect to the elongated surgical implement. The stop-ledge may also provide a reference or index point for a practitioner when assembling the components. The clip may releasably secure the guide which may tend to maintain the position of the proximal edge of the guide, for example, in abutment with the stop-ledge. The interaction of these features may facilitate coupling of the guide while allowing the guide to retain its shape during a procedure.

In some embodiments, the surgical implement may comprise a lumen or other passageway through the implement or a portion thereof. In some such embodiments, the knob may comprise a passageway through the knob, such as a central passageway. In some embodiments, a passageway through the knob may be surrounded by other components, for example, a hollow hub. Openings, passageways, and lumens disposed with the surgical implement, the knob, a hub, or other components may be in communication with each other such that they define an introduction passage for introduction of additional surgical implements or devices through the first surgical implement.

FIG. 1 is a side view of an assembly comprising a dilator 65 and a guide 10 with a clip 39 engaged to releasably secure the guide 10 to the dilator 65. For example, the clip 39 may be configured to engage a groove 56 of a knob 50 on the dilator 65 to releasably secure a shaft 13 or other portion of the guide 10 to the dilator 65. These and other features of the embodiment of FIG. 1 are further detailed below.

In some embodiments, such as the embodiment of FIG. 1, the guide 10 may be made of flexible material including materials which may be molded or otherwise formed with shape memory or the tendency to return to a particular configuration or geometry. The guide 10 may comprise an elongated shaft 13 and a tab 25 coupled to the elongated shaft 13. The elongated shaft 13 and tab 25 may be integral with the elongated shaft 13. The guide 10, including the elongated shaft 13 and tab 25, may comprise a single integrally formed component. In the illustrated embodiment, the dilator 65 is disposed within a portion of the elongated shaft 13 of the guide 10. The dilator 65 may have a knob 50 which may further comprise a hollow hub 55 at or adjacent the proximal end of the knob 50. The knob 50 and hollow hub 55 may comprise a through passage parallel longitudinally to and aligned with the dilator 65. It is within the scope of this disclosure to form the guide 10 at any length; in some embodiments the guide 10 may be from about 4 inches to about 24 inches long, for example, including from about 6 inches to about 20 inches, and from about 8 inches to about 18 inches long. The elongate shaft 13 of the guide 10, comprising a portion of the length of the guide 10, may be from about 1 inch to about 22 inches in length, including from about 3 inches to about 18 inches, and from about 5 inches to about 16 inches. The elongate shaft 13 may be configured with a passageway to receive any surgical implement or other component, for example, a catheter, a dilator, a trocar, a cannula, or any other surgical implement or device.

The elongate shaft 13 may define a slot 19, the slot 19 may be configured to allow for expansion and compression of the guide 10 and to allow for insertion and removal of surgical implements into and from the body. In some embodiments, the width of slot 19 may be larger or smaller depending on factors such as the diameter of elongate shaft 13, the size of the instrument the elongate shaft 13 is configured to surround, and so forth. The slot 19 may or may not extend along the entire length of the shaft 13. In the illustrated embodiment, the slot 19 extends the entire length of the elongate shaft 13.

In some embodiments, an elongated tab 25 extends from the elongate shaft 13. For example, in the illustrated embodiment, the elongated tab 25 extends from the proximal end of the elongate shaft 13. The elongated tab 25 may be utilized as a handle, providing grip for a user during insertion or removal of the guide 10, or removal or insertion of a surgical implement such as dilator 65 from or into the guide 10. Thus, the elongated tab 25 may be utilized to secure the guide 10 during insertion of the dilator 65, or other medical instrument, into the guide 10. While a rectangular configuration of the elongated tab 25 is depicted in the illustrated embodiment, many other shapes can be utilized, including an angled or a curved tab. In some embodiments the elongated tab 25 may be formed with sufficient structure or rigidity to facilitate introduction of the guide 10 into an opening in body tissue when a user is grasping the elongated tab 25. Alternatively or additionally, the elongated tab 25 can be flared, or otherwise shaped to interact with other elements of the assembly. For example, the elongated tab 25 may be flared to accommodate and surround the proximal knobs of various surgical implements. Furthermore, the elongated tab 25 may have one or more surfaces with a texture on all or a portion thereof.

The dilator 65 may have a tapered distal end portion that terminates at distal end 69. The knob 50 may be coupled to the dilator 65 at or adjacent a proximal end of the dilator 65. The knob 50, distal end portion, and other features of the dilator 65 may or may not be integrally formed. The knob 50 may have a hub, such as the integrally formed, hollow hub 55 of the illustrated embodiment. The hub 55 may define a passageway extending from an aperture 53, the aperture 53 and hub 55 configured to accommodate insertion of another medical implement or tool, such as a guidewire and the like, through the hub 55. The dilator 65 may thus comprise a lumen or passageway through the dilator 65. This passageway may extend along the entire length of the dilator 65, of any portion thereof. In the illustrated embodiment, the passageway extends from the hub 55 to an opening adjacent the distal end 69 of the dilator. This passageway may thus be configured such that the dilator 65 comprises a hollow tube; a guidewire or other surgical tool or device may thus be inserted via the aperture 53, pass through the dilator 65, and exit the dilator 65 through the opening in the distal end 69. The knob 50 may further comprise a circumferential groove 56 for engaging a distal portion of a strap 30, as further detailed below.

In the embodiment of FIG. 1, a strap 30 is rotatably coupled to the knob 50, such that the strap 30 is free to rotate with respect to the knob 50. In the illustrated embodiment, an integrally formed loop or ring 33 at the proximal end of the strap 30 is coupled to a portion of the knob 50. Other means or methods of coupling the strap 30 and knob 50 are within the scope of this disclosure, including coupling arrangements wherein the strap 30 is not necessary free to rotate with respect to the knob 50. The strap 30 may comprise an elastomeric material and may include a clip 39 at or adjacent the distal end thereof. In some embodiments, an assembly may comprise a pair of such straps is provided to facilitate both disengagement of the clip 39 from the hub 55 and to prevent inadvertent loss of the clip within the surgical field, for example.

A slot 45 may be provided in the strap 30. The slot 45 may be configured to accommodate a portion of elongated tab 25 of the guide 10, allowing a portion of the elongated tab 25 or other element to extend through the slot 45. In the embodiment of FIG. 1, the clip 39 is configured to engage the knob 50 in the circumferential groove 56 such that the clip 39 is releasably coupleable to the knob 50. In some embodiments, the groove 56 may or may not extend completely around the circumference of the knob 50. When the clip 39 is coupled to the knob 50, for example, through engagement of the clip 39 in the groove 56, a portion of the shaft 13, the elongated tab 25, or other portion of the guide 10 may be engaged between the clip 39 and the groove 56. For example, when a surgical implement is inserted into the guide 10, the shaft 13 (or other portion of the guide 10) may partially overlap circumferential groove 56. Engagement of the clip 39 in circumferential groove 56 may thus engage the shaft 13 (or other portion of the guide 10 which overlaps the groove 56). The clip 39 may therefore secure the guide 10 to the knob 50 such that guide 10 is fixed relative to the surgical implement.

FIG. 2 is a side view of an assembly comprising a trocar 66 and a guide 11 with a clip 40 engaged to releasably secure the guide 11 to the trocar 66, via securement of the clip 40 to a knob 51 in the illustrated embodiment. The assembly of FIG. 2, and various components thereof, resemble the assembly, and components thereof, as depicted in FIG. 1. Analogous disclosure given with respect to one assembly may be applied to the other and vice versa. The applicability of any portion of analogous disclosure given in connection with any embodiment described herein may be applied to any other embodiment.

The guide 11, of the embodiment of FIG. 2, may be made of flexible material, including material configured with shape memory, or the tendency to return to a set configuration. The guide 11 may comprise an elongate shaft 14 and a tab 26. The trocar 66 of the assembly is illustrated as disposed within the elongated shaft 14 of the guide 11. As with other embodiments described herein, the guide 11 may be of any length, including from about 4 inches to about 24 inches long with the elongated shaft 14 being from about 1 inch to about 22 inches long. Any of the length ranges given in connection with the guides of other embodiments disclosed herein also apply to the guide 11 of the embodiment of FIG. 2. The elongate shaft 14 may be configured to receive a catheter, a dilator, a trocar, a cannula, or other surgical implement.

The elongate shaft 14 may further comprise a slot 20 that may be configured to allow for expansion and compression of the guide 11 and may facilitate insertion and/or removal of surgical implements into or through the guide 11. The slot 20 may be sized depending on the diameter of the elongated shaft 14 or the size of a device configured to be disposed in the guide 11. The slot 20 may or may not extend along the entire length of the elongate shaft 14.

An elongated tab 26 may extend from the proximal end of the elongate shaft 14. The elongated tab 26 may be configured to serve as a handle, providing grip for a user during insertion or removal of the guide 11, and/or insertion or removal of the surgical implement to or from the guide 11. While a rectangular configuration is illustrated for the tab 26, many other shapes can be utilized, including an angled or a curved tab. The tab 26 may be formed with structure, geometry, or reinforcement configured to facilitate pushing the guide 11 into the tissue, or otherwise displacing the guide 11, through force applied to the tab 26. Alternatively or additionally, the tab 26 can be flared to accommodate and surround the one or more portions, such as proximal knobs, of various surgical implements. The tab 26 may have one or more surfaces with a texture on all or a portion thereof.

As illustrated in FIG. 2, the trocar 66 may be provided with a knob 51 at or adjacent the proximal end thereof. The knob 51 may further define a circumferential groove 57 as well as a stop-ledge such as stop-ledge 49 (FIG. 3) which may be configured to position the proximal end of the guide 11. As with groove 57, the stop-ledge 49 may or may not extend completely around the knob 51. A strap 31 may be rotatably coupled to the knob 51, such as via an integrally formed loop or ring 34 at the proximal end of the strap 31. In the illustrated embodiment, the strap 31 includes a clip 40 at the distal end thereof. In some embodiments, a pair of straps may be provided to facilitate disengagement of the clip 40 from the knob 51 of the surgical device and to prevent inadvertent loss of the clip within the surgical field, for example. A slot 46 may also be provided in the strap 31. The slot 46 may be configured to accommodate a portion of the elongated tab 26, the shaft 14, or other portion of the guide 11. As with the previous embodiment, the clip 40 may engage the knob 51 in a circumferential groove 57 to releasably couple the clip 40 to the knob 51 while engaging a portion of the guide 11 therebetween. Thus, when a surgical instrument is inserted into the guide 11, a portion of the guide 11 such as the shaft 14 may partially overlap circumferential groove 57. When clip 40 engages circumferential groove 57 and the overlapping portion of the guide 11, the clip 40 may secure the guide 11 to the knob 51 such that guide 11 is fixed relative to the surgical implement.

FIG. 3 is a partial view of a proximal end of the assembly of FIG. 2 with the clip 40 disengaged from the knob 51 of the trocar 66. In the view of FIG. 3, the proximal end of the guide 11 is illustrated receiving the trocar 66. The elongate shaft 14 and tab 26 of the guide 11 are also shown relative to the knob 51 of the trocar 66. In the illustrated configuration, the shaft 14 partially surrounds the knob 51. Further, a circumferential groove 57, which may be integrally formed in the knob 51, is shown. A proximal end portion of the shaft 14 may abut a rim or other portion of the knob 51, such as a rim that defines a portion of the groove 57. The tab 26 may extend through a slot 46 in the strap 31 in one assembled configuration. The strap 31, in turn, may again be rotatably coupled to the knob 51 by a ring 34 which may be integrally formed with the strap 31. In the configuration of FIG. 3, the clip 40 is shown disengaged from the knob 51.

FIG. 4 is a side view of an assembly comprising a cannula 67—with a knob 52 having an outwardly extending hollow hub 59—a guide 12, and a trocar 68; a clip 41 is engaged to releasably secure the guide 12 to the cannula 67. The guide 12, which may be made of flexible material such as a material configured with shape memory, may comprise an elongated shaft 15 and a tab 27. In the illustrated configuration, the elongated shaft 15 is shown receiving the cannula 67 therein. The guide 12 can be of any length, including from about 4 inches to about 24 inches long with the shaft 15 from about 1 inch to about 22 inches long. Any other length or range of lengths for any guide disclosed herein may be applied to the guide 12 of this embodiment. The shaft 15 may be configured to receive a catheter, a dilator, a trocar, a cannula, or other surgical implement or device in a passageway within the shaft 15.

The shaft 15 may further comprise a slot 21 that may be configured to allow for expansion and compression of the guide 12 and may facilitate insertion and/or removal of surgical implements into or through the guide 12. The slot 21 may be sized depending on the diameter of shaft 15 or the size of a device configured to be disposed in the guide 12. The slot 21 may or may not extend along the entire length of the shaft 15.

An elongated tab 27 may extend from the proximal end of the shaft 15. The elongated tab 27 may be configured to serve as a handle, providing grip for a user during insertion or removal of the guide 12, and/or to hold the guide while inserting or removing surgical implements from the guide 12. While a rectangular configuration is illustrated for the tab 27, many other shapes can be utilized, including an angled or a curved tab. The tab 27 may be formed with structure, geometry, or reinforcement configured to facilitate pushing the guide 12 into the tissue, or otherwise displacing the guide 12, through force applied to the tab 27. Alternatively or additionally, the tab 27 can be flared to accommodate and surround the one or more portions, such as proximal knobs, of various surgical implements. The tab 27 may have one or more surfaces with a texture on all or a portion thereof.

In the embodiment of FIG. 4, the cannula 67 comprises a knob 52 adjacent the proximal end thereof. The knob 52 of the illustrated embodiment comprises a hub 59, which may be integrally formed with the knob 52. The hub 59 comprises an aperture 54 (FIG. 5) which may be sized for receiving the trocar 68. The trocar may further comprise a cap 61. The cap 61 may comprise a gripping feature and may comprise a knob in some embodiments. In the illustrated configuration, the cap 61 extends from the proximal end of the assembly. The knob 52 may also define a circumferential groove 58. As with other embodiments, a strap 32 may be coupled to the knob 52, including embodiments wherein the strap 32 is rotatably coupled to the knob 52 by a ring 35. The ring 35 may be integrally formed with the strap 32. The strap 32 of the illustrated embodiment comprises an integrally formed clip 41 at the distal end of the strap 32. A slot 47 may be located in the strap 32 and may be configured to accommodate a portion of the elongated tab 27 of the guide 12. Further, the clip 41 may engage the knob 52, for example, by engaging the circumferential groove 58, to releasably attach the clip 41 to knob 52 such that the elongated tab 27, shaft 15, or other portion of the guide 12 is engaged between the clip 41 and the knob 52.

FIG. 5 is a partial view of a proximal end of the assembly of FIG. 4 with the trocar 68 removed from the cannula 67 and the clip 41 disengaged from the cannula 67. Thus, as compared to the configuration of FIG. 4, the trocar 68 (including the associated cap 61 portion) has been removed from the assembly in the configuration of FIG. 5. The proximal end of the guide 12 is shown receiving cannula 67. The shaft 15 and tab 27 of the guide are also illustrated. The shaft 15 of the guide 12 partially circumscribes the knob 52 including the circumferential groove 58 and a stop-ledge 70 in the configuration of FIG. 5. The proximal end of the shaft 15 of the guide 12 is positioned such that it abuts the stop-ledge 70. Additionally, the tab 27 is shown extending through the slot 47. In the illustrated embodiment, the strap 32 is rotatably attached to the knob 52 by the ring 35. As with other embodiments, the ring 35 may or may not be integral with the strap 32. The clip 41 is shown disengaged from the knob 52 and groove 58 in the illustrated configuration.

The devices, components, and assemblies as disclosed herein may be utilized in a wide variety of procedures. Exemplary procedures may include minimally invasive surgeries, vascular access procedures, catheter placement procedures, and so forth. An exemplary procedure is disclosed below referencing the components of the embodiment of FIGS. 1 and 2. It is within the scope of this disclosure to utilize any embodiment disclosed herein in any procedure described herein.

In one exemplary procedure, a practitioner may dispose the dilator 65 within the guide 10. The guide 10 may generally conform to the shape of the dilator 65 due to the memory characteristics of the guide 10 and the slot 19 in the guide 10. In other words, the memory characteristics of the guide 10 may cause the guide to tend to return to a generally cylindrical shape, with the slot 19 allowing the diameter of the cylindrical shape to be expanded when the dilator 65 is disposed within the guide 10.

The practitioner may position the guide 10 with respect to the dilator 65 by aligning a portion of the guide 10 with the groove 56. The groove 56 may define a proximal edge which functions as a stop-ledge (such as 49 of FIG. 3 and 70 of FIG. 5). The groove 56 may thus provide a positive stop due to the interaction between a proximal edge of the guide 10 and the groove 56, or may simply provide a reference point for the positioning of the guide 10.

When the guide 10 is disposed in a desired position with respect to the dilator 65, the practitioner may then couple the guide 10 to the dilator 65 by engaging the clip 39 with a portion of the dilator 65 and engaging a portion of the guide between the clip 39 and the dilator 65. In the illustrated embodiment, the clip 39 is engaged with the groove 56. The practitioner may also extend the tab 25 of the guide 10 through the slot 45 on the strap 30 in order to facilitate displacement of the guide 10 with respect to the dilator 65. The tab 25, extending through the slot 45 in the strap 30, may provide a handle for the practitioner to manipulate the guide 10 while leaving the portion of the guide 10 which is engaged by the clip 39 free of interference by the practitioner's hands.

In embodiments wherein the strap 30 is rotatably coupled to the knob 50, the practitioner may further rotate the strap 30 to align the slot 45 in the strap 30 with the tab 25 without displacing the guide 10 with respect to the dilator 65. The practitioner may also advance the dilator 65 and guide 10 into the patient's body. In some instances, abutment between the guide 10 and a portion of the groove 56 may facilitate such advancement. Further, the practitioner may advance the guide 10 by displacing the tab 25 when the guide 10 and dilator 65 are not coupled.

After coupling and insertion into the body of the dilator 65 and guide 10, the practitioner may decouple the guide 10 from the dilator 65 by decoupling the clip 39 from the groove 56. The strap 30 may prevent inadvertent loss of the clip 39 when disengaged. The guide 10 may be withdrawn from the body 10 by displacement of the tab 25 while the position of the dilator 65 is maintained. In some instances the tab 25 and guide 10 may be retracted on a parallel plane to the dilator 65, thus facilitating removal of the guide 10 without disturbing the dilator 65.

Without further elaboration, it is believed that one skilled in the art can use the preceding description to utilize the present disclosure to its fullest extent. The examples and embodiments disclosed herein are to be construed as merely illustrative and exemplary, and not a limitation of the scope of the present disclosure in any way. It will be apparent to those having skill in the art that changes may be made to the details of the above-described embodiments without departing from the underlying principles of the disclosure herein. It is intended that the scope of the invention be defined by the claims appended hereto and their equivalents.

The invention claimed is:

1. A surgical implement extending from a proximal end to a distal end, the surgical implement comprising:
   a knob disposed adjacent the proximal end of the surgical implement;
   a groove defining a stop-ledge disposed adjacent the knob;
   a strap extending between a first end and a second end, the first end rotatably coupled to the knob; and
   a clip coupled to the second end of the strap, the clip configured to releasably engage the groove to releasably couple the clip to the groove, and wherein the clip is configured to couple a portion of a secondary device to the surgical implement at a position between the clip and the groove when the clip is engaged to the groove;
   wherein the strap comprises a strap slot disposed in the strap, the strap slot configured to receive and surround an elongate tab of the secondary device.

2. The surgical implement of claim 1, wherein the first end of the strap comprises a ring rotatably coupled to the knob.

3. The surgical implement of claim 2, wherein the strap, the ring, and the clip comprise a single integral component.

4. The surgical implement of claim 3, wherein the single integral component is formed from an elastomeric material.

5. The surgical implement of claim 1, wherein the surgical implement comprises one of a cannula, a trocar, and a dilator.

6. A surgical implement assembly, comprising:
   a first surgical implement extending from a proximal end to a distal end;
   a knob coupled adjacent the proximal end of the first surgical implement;
   a groove adjacent the knob, the groove defining a stop-ledge;
   a strap extending between a first end and a second end, the first end coupled to the knob, the strap comprising a strap slot disposed in the strap;
   a clip coupled to the second end of the strap, the clip configured to releasably engage the groove to releasably couple the clip to the groove; and a second surgical implement configured to be releasably engaged between the clip and the groove, the second surgical implement comprising an elongate tab configured to extend through the strap slot when the second surgical implement is engaged between the clip and the groove.

7. The surgical implement assembly of claim 6, wherein the second surgical implement comprises a guide.

8. The surgical implement assembly of claim 7, wherein the guide comprises a slot along a longitudinal direction of the guide.

9. The surgical implement assembly of claim 8, wherein the guide comprises a memory material configured to conform to a portion of the first surgical implement.

10. The surgical implement assembly of claim 6, wherein the stop-ledge is positioned to abut a first portion of the second surgical implement when the second surgical implement is engaged between the clip and the groove.

11. The surgical implement assembly of claim 6, wherein the first surgical implement comprises one of a cannula, a trocar, and a dilator.

\* \* \* \* \*